United States Patent
Weiser et al.

(10) Patent No.: US 10,941,238 B2
(45) Date of Patent: Mar. 9, 2021

(54) VISCOELASTIC ELEMENT BASED ON A POLYURETHANE FOAM

(71) Applicant: Covestro Deutschland AG, Leverkusen (DE)

(72) Inventors: Marc-Stephan Weiser, Kürten-Dürscheid (DE); Sascha Plug, Leverkusen (DE); Sebastian Doerr, Düsseldorf (DE); Jeff Motley, Staffordshire (GB)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/650,424

(22) PCT Filed: Oct. 2, 2018

(86) PCT No.: PCT/EP2018/076852
§ 371 (c)(1),
(2) Date: Mar. 25, 2020

(87) PCT Pub. No.: WO2019/068732
PCT Pub. Date: Apr. 11, 2019

(65) Prior Publication Data
US 2020/0377643 A1   Dec. 3, 2020

(30) Foreign Application Priority Data

Oct. 7, 2017 (EP) .................................... 17195351

(51) Int. Cl.
| | |
|---|---|
| *C08G 18/40* | (2006.01) |
| *A61F 11/08* | (2006.01) |
| *C08G 18/12* | (2006.01) |
| *C08G 18/34* | (2006.01) |
| *C08G 18/48* | (2006.01) |
| *C08J 9/02* | (2006.01) |

(52) U.S. Cl.
CPC ............ *C08G 18/409* (2013.01); *A61F 11/08* (2013.01); *C08G 18/12* (2013.01); *C08G 18/345* (2013.01); *C08G 18/348* (2013.01); *C08G 18/4841* (2013.01); *C08J 9/02* (2013.01); *C08J 2207/10* (2013.01); *C08J 2375/04* (2013.01)

(58) Field of Classification Search
CPC .............. C08G 18/409; C08G 18/4841; C08G 18/348; C08G 18/12; C08G 18/345; C08J 9/02; C08J 2375/04; C08J 2207/10; A61F 11/08
See application file for complete search history.

(56) References Cited

U.S. PATENT DOCUMENTS

| | | |
|---|---|---|
| 2011/0184080 A1 | 7/2011 | Schonberger et al. |
| 2015/0004389 A1* | 1/2015 | Corinti ............... C08G 18/1833 428/220 |
| 2016/0200855 A1 | 7/2016 | Casati et al. |

OTHER PUBLICATIONS

Ullmanns Encyclopädie der technischen Chemie [Ullmann's Encyclopedia of Industrial Chemistry], 4th edition, vol. 19, Verlag Chemie, Weinheim p. 31-38.
International Search Report, PCT/EP2018/076852, dated Jan. 28, 2019, Authorized officer: Martin Bergmeier.

* cited by examiner

*Primary Examiner* — Patrick D Niland
(74) *Attorney, Agent, or Firm* — Jed C. Benson

(57) ABSTRACT

The present invention relates to a viscoelastic element comprising a polyurethane foam, wherein the polyurethane foam can be obtained by reacting at least one isocyanate-functional prepolymer (VI) in the presence of a special polyurethane urea dispersion (V2), wherein the reaction of the prepolymer (VI) takes place in the presence of the polyurethane urea (V2) with a medium containing isocyanate-reactive groups. The invention also relates to a method for producing the viscoelastic element and to the use thereof.

18 Claims, No Drawings

VISCOELASTIC ELEMENT BASED ON A POLYURETHANE FOAM

CROSS-REFERENCE TO RELATED APPLICATION

This application is a national stage application under 35 U.S.C. § 371 of PCT/EP2018/076852, filed Oct. 2, 2018, which claims the benefit of European Application No. 17195351, filed Oct. 7, 2017, each of which is incorporated herein by reference.

FIELD

The present invention relates to a viscoelastic element including a polyurethane foam, wherein the polyurethane foam is obtainable by reaction of at least one isocyanate-functional prepolymer (V1) in the presence of a specific polyurethaneurea dispersion (V2), wherein the reaction of the prepolymer (V1) in the presence of the polyurethaneurea (V2) takes place with a medium containing isocyanate-reactive groups. The invention further relates to a process for producing the viscoelastic element and to the use thereof.

BACKGROUND

Polyurethane foams are known as wound dressings for medical applications. These foams preferably have a high absorption rate and retention rate for water, as shown in EP 2 143 744 A1.

Although the foams obtained according to EP 2 143 744 A1 are manufactured from a medically approved raw material, they are unsuitable for use as sound insulation/earplugs; more particularly, they show excessively rapid recovery capacity on compression. For use as sound insulation/earplugs, it is important that the foam recovers only gradually to its shape after compression or can adapt to other spatial circumstances such as the inner ear.

SUMMARY

It is an object of the present invention to at least partly overcome at least one disadvantage of the prior art.

It is a further object of the present invention to produce a viscoelastic element, for example based on medically approved raw materials, such as the materials described in EP 2 143 744 A1, and to modify these in such a way that slower recovery characteristics are achieved by comparison.

It is additionally an object of the present invention to provide a viscoelastic element having optimized recovery time.

It is a further object of the present invention to achieve maximum wear comfort of an earplug, in the form of a viscoelastic element, for example in the ear of a user.

It is another object of the present invention to provide a process for producing a viscoelastic element that enables production of the element in few steps with maximum conservation of resources. It is an additional object of the present invention to provide a process for producing a viscoelastic element which is performable at room temperature and standard pressure.

It is another object of the present invention to provide a viscoelastic element that is suitable for use in the auditory canals of users, especially for minimization of noise.

It is an additional object of the present invention to provide a kit that enables a simple means of production of the viscoelastic element.

The invention firstly relates to a viscoelastic element, also referred to hereinafter as product, including a polyurethane foam, obtainable by reaction of at least the following components:

(V1) an isocyanate-functional prepolymer obtainable by reaction of at least the following components:
   V1A) aliphatic diisocyanates with
   V1B) di- to hexafunctional polyalkylene oxides having an ethylene oxide content of 50 to 100 mol %, based on the total amount of oxyalkylene groups present, in the presence of
(V2) a polyurethaneurea dispersion, where the polyurethaneurea is obtainable by reacting at least
   V2A) an aliphatic polyisocyanate component having an average isocyanate functionality of $\geq 1.8$ and $\leq 2.6$,
   V2B) a polymeric polyether polyol component,
   V2C) an amino-functional chain extender component having at least 2 isocyanate-reactive amino groups, containing at least one amino-functional compound C1) that does not have any ionic or ionogenic groups and/or an amino-functional compound C2) that has ionic or ionogenic groups,
   V2D) optionally further hydrophilizing components different than C2),
   V2E) optionally hydroxy-functional compounds having a molecular weight of 62 to 399 g/mol,
   V2F) optionally at least one further polymeric polyol different than V2B),
   V2G) a compound having exactly one isocyanate-reactive group or a compound having more than one isocyanate-reactive group, where only one of the isocyanate-reactive groups reacts with the isocyanate groups present in the reaction mixture under the reaction conditions chosen, and
   V2H) optionally an aliphatic polyisocyanate component having an average isocyanate functionality of $\geq 2.6$ and $\leq 4$,
wherein the reaction of the prepolymer (V1) in the presence of the polyurethaneurea (V2) takes place with a medium containing isocyanate-reactive groups.

DETAILED DESCRIPTION

Viscoelasticity refers to partly elastic, partly viscous material characteristics. Viscoelastic substances thus combine features of liquids and solids. The effect is time-, temperature- and frequency-dependent and occurs in the case of polymeric melts and solids, for example plastics, but also other materials.

All liquids and solids can be viewed as viscoelastic materials if their storage modulus and loss modulus, G' and G", or their loss factor tan $\delta = G''/G'$, can be reported. In the case of liquids of ideal viscosity (Newtonian fluid), the storage modulus is very small compared to the loss modulus; in the case of solids of ideal elasticity, which obey Hooke's law, the loss modulus is very small compared to the storage modulus. Viscoelastic materials have both a measurable storage modulus and a measurable loss modulus. If the storage modulus is greater than the loss modulus, they are referred to as solids, and otherwise as liquids. The viscoelastic element is preferably a solid having both a measurable storage modulus and a measurable loss modulus. The viscoelastic element preferably has a greater storage modulus than loss modulus. The viscoelastic element preferably has a storage modulus greater than the loss modulus by a factor within a range from 1.1 to 7, or preferably within a range from 1.5 to 6.5, or preferably within a range from 2 to 6.

The loss factor is thus a measure of the damping of a viscoelastic body or viscoelastic element. The loss factor tan δ of the element of the invention under compressive or tensile deformation in the direction of action is preferably 0.15 to 0.50, or preferably 0.16 to 0.45, or preferably 0.17 to 0.40, or preferably 0.17 to 0.35, measured to DIN EN ISO 6721-1 Determination of dynamic mechanical properties (using oscillation mode I, non-resonant, module type $G_{to}$, oscillation mode IV and Part 2).

It has been found that, surprisingly, based on the components V1) and V2) mentioned, it was possible to obtain products that have soft, pleasant tactile properties on the one hand and viscoelastic properties on the other hand. The effect of the viscoelastic properties is that the viscoelastic element, on deformation, does not have spontaneous recovery but has retarded recovery to its original shape when the deformation force is released. This effect, referred to as viscoelastic, can be utilized in a wide variety of uses of the element of the invention. For example, it can serve to give cushions, mattresses, seats or similar structures a very soft appearance, but especially to fit extremely well to the geometry of the cavity having been compressed and inserted into a cavity, without exerting pressure on the cavity walls.

As component V1A) it is possible to use any diisocyanate that the person skilled in the art would select for the purpose. Preferably, the aliphatic diisocyanates V1A) have a molar mass of 140 to 278 g/mol.

Examples of suitable aliphatic diisocyanates V1A) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, preference being given to hexamethylene diisocyanate, isophorone diisocyanate, butylene diisocyanate and bis(isocyanatocyclohexyl)methane. Particular preference is given to butylene diisocyanate, hexamethylene diisocyanate, isophorone diisocyanate, very particular preference to hexamethylene diisocyanate and isophorone diisocyanate.

As component V1B) it is possible to use any polyalkylene oxides that the person skilled in the art would select for the purpose.

It is also advantageous when the di- to hexafunctional polyalkylene oxides V1B) have an OH number of 22.5 to 112.

The polyalkylene oxides have an ethylene oxide content of 50 to 100 mol %, preferably of 55 to 95 mol %, or preferably of 60 to 80 mol %, based on the total amount of the oxyalkylene groups present.

The polyalkylene oxides typically have number-average molecular weights of 1000 to 15 000 g/mol, preferably of 1500 to 12 000 g/mol, or preferably of 2000 to 10 000 g/mol, or preferably of 2500 to 9000 g/mol, or preferably of 3000 to 8000 g/mol.

In addition, the polyalkylene oxides of component V1B) preferably have OH functionalities of 2 to 6, more preferably of 3 to 6, especially preferably of 3 to 4.

Suitable polyalkylene oxides are, for example, copolymers of ethylene oxide and propylene oxide.

It is also particularly preferable when the polyalkylene oxides are started on the basis of polyols or amines Suitable initiators are glycerol, trimethylolpropane (TMP), sorbitol, pentaerythritol, triethanolamine, ammonia or ethylenediamine.

In the preparation of the isocyanate-functional prepolymers V1), the ratio of the polyalkylene oxides V1B) to the low molecular weight, aliphatic diisocyanates V1A) is typically adjusted such that, for every 1 mol of OH groups of the polyalkylene oxides V1B), there are 2 to 20 mol, preferably 2 to 10 mol and more preferably 5 to 10 mol of NCO groups of the low molecular weight, aliphatic diisocyanate V1A).

The prepolymers are preferably prepared in the presence of urethanization catalysts such as tin compounds, zinc compounds, amines, guanidines or amidines, or in the presence of allophanatization catalysts such as zinc compounds.

The reaction of the polyalkylene oxides V1B) with the diisocyanates V1A) to give the prepolymer V1) is typically effected at 25 to 140° C., preferably at 60 to 100° C.

If an excess of diisocyanate V1A) was used in the reaction, the unconverted residue is then preferably removed by thin-layer distillation.

Before, during and after the reaction of the diisocyanates V1A) with the polyalkylene oxides V1B) or the distillative removal of the excess diisocyanate, it is possible to add acidic or alkylating stabilizers such as benzoyl chloride, isophthaloyl chloride, methyl tosylate, chloropropionic acid, HCl or antioxidants such as di-tert-butylcresol or tocopherol.

Preferably, the prepolymers V1) used have a residual monomer content of less than 0.5% by weight, preferably less than 0.4% by weight, or preferably less than 0.3% by weight, based on the total weight of the prepolymer. This content can be achieved via appropriately chosen use amounts of the diisocyanates V1A) and the polyalkylene oxides V1B). However, preference is given to the use of the diisocyanate V1A) in excess and with subsequent, preferably distillative, removal of unconverted monomers.

The NCO content of the isocyanate-functional prepolymers V1) is preferably 1.5% to 4.5% by weight, more preferably 1.5% to 3.5% by weight and most preferably 1.5% to 3.0% by weight, based on the total weight of the prepolymer.

An aqueous dispersion in the context of the present invention is a heterogeneous mixture of a particulate solid (disperse phase) in a water-containing liquid phase (dispersion medium). Preference is given to a dispersion in which the average diameter of the disperse phase determined by laser correlation spectroscopy is 1 to 1000 nm, preferably 2 to 800 nm, more preferably 5 to 500 nm and especially preferably 20 to 400 nm. It is likewise preferable when the dispersion medium consists exclusively of water.

Polyurethaneureas in the context of the invention are polymeric compounds having at least two, preferably at least three, urethane-containing repeat units:

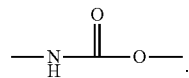

According to the invention, the polyurethaneureas, by virtue of their preparation, also have repeat units that contain urea groups

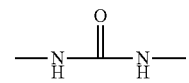

as formed particularly in the reaction of isocyanate-terminated prepolymers with amino-functional compounds.

Ionogenic groups in the context of this invention are understood to mean those functional groups that are capable of forming ionic groups, for example by neutralization with a base.

Component V2A) may be any polyisocyanate that the person skilled in the art would use for the purpose. Polyisocyanates suitable with preference as component V2A) are especially the aliphatic polyisocyanates known per se to the person skilled in the art that have an average isocyanate functionality of ≥1.8 and ≤2.6, preferably of ≥1.9 and ≤2.5. The term "aliphatic" also includes cycloaliphatic and/or araliphatic polyisocyanates.

Mean isocyanate functionality is understood to mean the average number of isocyanate groups per molecule.

Preferred polyisocyanates are those in the molecular weight range from 140 to 336 g/mol. These are more preferably selected from the group consisting of 1,4-diisocyanatobutane (BDI), pentane 1,5-diisocyanate (PDI), 1,6-diisocyanatohexane (HDI), 1,3-bis(isocyanatomethyl)benzene (xylylene 1,3-diisocyanate, XDI), 1,4-bis(isocyanatomethyl)benzene (xylylene 1,4-diisocyanate, XDI), 1,3-bis(1-isocyanato-1-methylethyl)benzene (TMXDI), 1,4-bis(1-isocyanato-1-methylethyl)benzene (TMXDI), 4-isocyanatomethyloctane 1,8-diisocyanate (trisisocyanatononane (TIN)), 2-methyl-1,5-diisocyanatopentane, 1,5-diisocyanato-2,2-dimethylpentane, 2,2,4- or 2,4,4-trimethyl-1,6-diisocyanatohexane, 1,10-diisocyanatodecane, and the cycloaliphatic diisocyanates 1,3- or 1,4-diisocyanatocyclohexane, 1,4-diisocyanato-3,3,5-trimethylcyclohexane, 1,3-diisocyanato-2(4)-methylcyclohexane, 1-isocyanato-3,3,5-trimethyl-5-isocyanatomethylcyclohexane (isophorone diisocyanate, IPDI), 1-isocyanato-1-methyl-4(3)isocyanatomethylcyclohexane, 1,8-diisocyanato-p-menthane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 4,4'- and/or 2,4'-diisocyanatodicyclohexylmethane, 4,4'-diisocyanato-3,3'-dimethyldicyclohexylmethane, 4,4'-diisocyanato-3,3',5,5'-tetramethyldicyclohexylmethane, 1,3-diisocyanatoadamantane, and 1,3-dimethyl-5,7-diisocyanatoadamantane or any mixtures of such isocyanates. The polyisocyanates are most preferably selected from butylene 1,4-diisocyanate, pentamethylene 1,5-diisocyanate (PDI), hexamethylene 1,6-diisocyanate (HDI), isophorone diisocyanate (IPDI), 2,2,4- and/or 2,4,4-trimethylhexamethylene diisocyanate, the isomeric bis(4,4'-isocyanatocyclohexyl)methanes or mixtures thereof with any isomer content (H12-MDI), cyclohexylene 1,4-diisocyanate, 4-isocyanatomethyloctane 1,8-diisocyanate (nonane triisocyanate) and alkyl 2,6-diisocyanatohexanoates (lysine diisocyanates) having C1-C8-alkyl groups.

As well as the aforementioned polyisocyanates, it is also possible to use modified diisocyanates having an average isocyanate functionality of ≥2 and ≤2.6, with uretdione, isocyanurate, urethane, allophanate, biuret, iminooxadiazinedione or oxadiazinetrione structure, and mixtures of proportions of these and/or the above.

Preference is given to polyisocyanates or polyisocyanate mixtures of the aforementioned type having exclusively aliphatically or cycloaliphatically bonded isocyanate groups or mixtures of these and an average NCO functionality of the mixture of ≥1.8 and ≤2.6 and more preferably ≥2.0 and ≤2.4.

More preferably, the organic polyisocyanate component V2A) contains an aliphatic or cycloaliphatic polyisocyanate selected from HDI, IPDI and/or H12-MDI or the modification products thereof, most preferably selected from HDI and/or IPDI.

In an especially preferred variant, IPDI and HDI are present in a mixture as component V2A).

The weight ratio of IPDI:HDI here is preferably in the range from 1.05 to 10, more preferably in the range from 1.1 to 5, and most preferably in the range from 1.1 to 1.5.

Preferably, the polyurethaneurea used in accordance with the invention is prepared using ≥5% and ≤40% by weight of component V2A) and more preferably ≥10% and ≤35% by weight of component V2A), based in each case on the total mass of the polyurethaneurea.

Preferably, the polyurethaneurea is also prepared using component V2H), an aliphatic polyisocyanate component having an average isocyanate functionality (average number of isocyanate groups per molecule) of ≥2.6 and ≤4, preferably ≥2.8 and ≤3.8. Component V2H) is preferably used in a mixture with component V2A).

Particularly suitable components V2H) are oligomeric diisocyanates having a functionality of ≥2.6 and ≤4, preferably ≥2.8 and ≤3.8, having isocyanurate, urethane, allophanate, biuret, iminooxadiazinedione or oxadiazinetrione structure. Most preferably, V2H) contains isocyanurate structures.

More preferably, the organic polyisocyanate component V2H) consists of an aliphatic or cycloaliphatic polyisocyanate oligomer based on HDI, IPDI and/or H12-MDI, most preferably based on HDI.

The molar ratio of the NCO groups from component V2A) to component V2H) is preferably 100:0.5 to 100:50, more preferably 100:2 to 100:15 and most preferably 100:3 to 100:8.

Preferably, the polyurethaneurea used in accordance with the invention is prepared using ≥0% and ≤10% by weight of component V2H) and more preferably ≥0.1% and ≤3% by weight of component V2H), based in each case on the total mass of the polyurethaneurea.

The polymeric polyetherpolyols used in accordance with the invention as component V2B) preferably have number-average molecular weights of ≥500 and ≤8000 g/mol, determined via gel permeation chromatography versus polystyrene standard in tetrahydrofuran at 23° C., more preferably ≥400 and ≤6000 g/mol, and especially preferably ≥600 and ≤3000 g/mol, and/or OH functionalities of preferably ≥1.5 and ≤6, more preferably ≥1.8 and ≤3, especially preferably ≥1.9 and ≤2.1.

The expression "polymeric" polyetherpolyols here means more particularly that the polyols mentioned have at least three, more preferably at least four, repeat units bonded to one another.

Number-average molecular weight is determined in the context of this application by gel permeation chromatography (GPC) in tetrahydrofuran at 23° C., unless stated otherwise. The procedure here is in accordance with DIN 55672-1: "Gel permeation chromatography, Part 1—Tetrahydrofuran as eluent" (SECurity GPC System from PSS Polymer Service, flow rate 1.0 ml/min; columns: 2×PSS SDV linear M, 8×300 mm, 5 μm; RID detector). Polystyrene samples of known molar mass are used for calibration. The number-average molecular weight is calculated with software support. Baseline points and evaluation limits are fixed according to DIN 55672 Part 1.

Suitable polyetherpolyols are, for example, the addition products, known per se, of styrene oxide, ethylene oxide, propylene oxide, butylene oxide and/or epichlorohydrin onto di- or polyfunctional starter molecules. Polyalkylene glycols in particular, such as polyethylene glycols, polypropylene glycols and/or polybutylene glycols, are employable, especially with the abovementioned preferred molecular weights. Suitable starter molecules used may be any compounds known from the prior art, for example water, butyldiglycol, glycerol, diethylene glycol, trimethylolpropane, propylene glycol, sorbitol, ethylenediamine, triethanolamine, butane-1,4-diol.

In a preferred embodiment of the product, component V2B) contains or consists of poly(tetramethylene glycol) polyetherpolyols (such as (HO—(CH$_2$—CH$_2$—CH$_2$—CH$_2$—O)$_x$—H).

Suitable poly(tetramethylene glycol) polyetherpolyols are obtainable, for example, by polymerization of tetrahydrofuran by means of cationic ring opening.

Preferably, component V2B) contains or consists of a mixture of poly(tetramethylene glycol) polyetherpolyols, where the poly(tetramethylene glycol) polyetherpolyols differ in their number-average molecular weights.

Further preferably, component V2B) contains a mixture of poly(tetramethylene glycol) polyetherpolyols I having a number-average molecular weight $M_n$ within a range from ≥400 and ≤1500 g/mol, more preferably within a range from ≥600 and ≤1200 g/mol, most preferably within a range of 1000 g/mol, and poly(tetramethylene glycol) polyetherpolyols II having a number-average molecular weight $M_n$ within a range from ≥1500 and ≤8000 g/mol, more preferably within a range from ≥1800 and ≤3000 g/mol, most preferably of 2000 g/mol.

The weight ratio of the poly(tetramethylene glycol) polyetherpolyols I to the poly(tetramethylene glycol) polyetherpolyols II is preferably in the range from 0.1 to 10, more preferably in the range from 0.2 to 10, most preferably in the range from 1 to 6.

According to the invention, the polyurethaneurea is prepared using an amino-functional chain extender component V2C) having at least 2 isocyanate-reactive amino groups, containing at least one amino-functional compound C1) that does not have any ionic or ionogenic groups and/or an amino-functional compound C2) that has ionic or ionogenic groups.

Preferably, the amino-functional chain extender component V2C) has isocyanate-reactive amino groups within a range from 2 to 4, or preferably within a range from 2.05 to 3, or preferably within a range from 2.1 to 2.3, or preferably of 2. If more than 2 isocyanate-reactive amino groups are present in the amino-functional chain extender component V2C), at least one of the more than 2 isocyanate-reactive amino groups has a lower reactivity toward isocyanate groups than the other two isocyanate-reactive amino groups. The particular effect of this is that, even with a number of more than 2 isocyanate-reactive amino groups, mainly a chain extension takes place and a lower degree of crosslinking of the available isocyanate groups.

The amino-functional compounds of component V2C) component are preferably selected from primary and/or secondary diamines. More particularly, the amino-functional compounds V2C) comprise at least one diamine.

The amino-functional component V2C) preferably comprises at least one amino-functional compound C2) having ionic and/or ionogenic groups.

The amino-functional component V2C) preferably comprises both amino-functional compounds C2) having an ionic and/or ionogenic group and amino-functional compounds C1) having no ionic or ionogenic group.

For example, components C1) used may be organic di- or polyamines, for example ethylene-1,2-diamine, 1,2- and 1,3-diaminopropane, 1,4-diaminobutane, 1,6-diaminohexane, isophoronediamine (IPDA), isomer mixture of 2,2,4- and 2,4,4-trimethylhexamethylenediamine, 2-methylpentamethylenediamine, diethylenetriamine, 4,4-diaminodicyclohexylmethane and/or dimethylethylenediamine or mixtures of at least two of these.

Preferably, component C1) is selected from the group consisting of ethylene-1,2-diamine, bis(4-aminocyclohexyl)methane, 1,4-diaminobutane, IPDA, ethanolamine, diethanolamine and diethylenetriamine or a mixture of at least two of these.

Further preferably, component C1) contains ≥75 mol %, more preferably ≥80 mol %, even more preferably ≥85 mol %, further preferably ≥95 mol % and still further preferably 100 mol % of ethylene-1,2-diamine or IPDA or a mixture of ethylene-1,2-diamine and IPDA, where the sum total of the two amines in relation to the total amount of C1) is preferably within the ranges mentioned. Preferably, component C1) contains ≥75 mol %, more preferably ≥80 mol %, even more preferably ≥85 mol %, further preferably ≥95 mol % and still further preferably 100 mol % of ethylene-1,2-diamine.

Preferably, the hydrophilizing component C2) comprises at least one anionically hydrophilizing compound. Further preferably, the hydrophilizing component C2) includes an anionically hydrophilizing compound to an extent of at least 80% by weight, or preferably to an extent of at least 90% by weight, based on the total weight of component C2). More preferably, component C2) consists of exclusively anionically hydrophilizing compounds.

Suitable anionically hydrophilizing compounds contain at least one anionic or ionogenic group that can be converted to an anionic group. Further preferably, suitable anionically hydrophilizing compounds have at least two amino groups and more preferably two amino groups. More preferably, the hydrophilizing component C2) comprises or consists of an anionically hydrophilizing compound having at least one anionic or ionogenic group and at least two amino groups.

Suitable anionically hydrophilizing compounds as component C2), also called hydrophilizing agents C2) hereinafter, preferably contain a sulfonic acid or sulfonate group, more preferably a sodium sulfonate group. Suitable anionically hydrophilizing compounds as component C2) are especially the alkali metal salts of the mono- and diaminosulfonic acids. Examples of such anionic hydrophilizing agents are salts of 2-(2-aminoethylamino)ethanesulfonic acid, N-(propyl or butyl)ethylenediaminesulfonic acid or propylene-1,2- or -1,3-diamine-β-ethylsulfonic acid or mixtures of at least two of these.

Particularly preferred anionic hydrophilizing agents C2) are those that contain sulfonate groups as ionic groups and two amino groups, such as the salts of 2-(2-aminoethylamino)ethylsulfonic acid and propylene-1,3-diamine-β-ethylsulfonic acid. Very particular preference is given to using 2-(2-aminoethylamino)ethylsulfonic acid or salts thereof as anionic hydrophilizing agent C2).

The anionic group in component C2) may optionally also be a carboxylate or carboxylic acid group. In that case, component C2) is preferably selected from diaminocarboxylic acids. In this alternative embodiment, however, the carboxylic acid-based components C2) have to be used in higher concentrations compared to those components C2) bearing sulfonate or sulfonic acid groups. More preferably, therefore, the polyurethaneurea is prepared using no hydrophilizing compounds bearing exclusively carboxylate groups as anionic groups of component C2).

Preferably, the polyurethaneurea used in accordance with the invention is prepared using within a range of ≥0.1% and ≤10% by weight of component C2) and more preferably within a range of ≥0.5% and ≤4% by weight of component C2), based in each case on the total mass of the polyurethaneurea.

Hydrophilization can also be accomplished using mixtures of anionic hydrophilizing agents C2) and further hydrophilizing agents V2D) that are different than C2).

Suitable further hydrophilizing agents V2D) are, for example, nonionic hydrophilizing compounds D1) and/or hydroxy-functional ionic or ionogenic hydrophilizing agents D2). Preferably, component V2D) comprises nonionically hydrophilizing components D1).

Suitable hydroxy-functional ionic or ionogenic hydrophilizing agents as component D2) are, for example, hydroxycarboxylic acids such as mono- and dihydroxycarboxylic acids, such as 2-hydroxyacetic acid, 3-hydroxypropanoic acid, 12-hydroxy-9-octadecanoic acid (ricinoleic acid), hydroxypivalic acid, lactic acid, dimethylolbutyric acid and/or dimethylolpropionic acid or mixtures of at least two of these. Preference is given to hydroxypivalic acid, lactic acid and/or dimethylolpropionic acid, particular preference to dimethylolpropionic acid. Preference is given to using no hydroxy-functional ionic or ionogenic hydrophilizing agents D2), especially preferably no hydrophilizing agents having carboxylate and hydroxyl groups, for example dimethylolpropionic acid. Preferably, the amount of hydroxy-functional ionic or ionogenic hydrophilizing agents D2) is present in the polyurethaneurea within a range from 0% to 1% by weight, or preferably within a range from 0% to 0.5% by weight, based on the total mass of the polyurethaneurea.

Suitable nonionically hydrophilizing compounds as component V2D) are, for example, polyoxyalkylene ethers having isocyanate-reactive groups, such as hydroxyl, amino or thiol groups. Preference is given to monohydroxy-functional polyalkylene oxide polyether alcohols having a statistical average of 5 to 70, preferably 7 to 55, ethylene oxide units per molecule, as obtainable in a manner known per se by alkoxylation of suitable starter molecules (for example in Ullmanns Encyclopadie der technischen Chemie [Ullmann's Encyclopedia of Industrial Chemistry], 4th edition, volume 19, Verlag Chemie, Weinheim p. 31-38). These are either pure polyethylene oxide ethers or mixed polyalkylene oxide ethers and they contain at least 30 mol %, preferably at least 40 mol %, based on all alkylene oxide units present, of ethylene oxide units.

Particularly preferred nonionic compounds are monofunctional mixed polyalkylene oxide polyethers having 40 to 100 mol % of ethylene oxide units and 0 to 60 mol % of propylene oxide units.

Suitable starter molecules for such nonionic hydrophilizing agents are especially saturated monoalcohols such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, for example diethylene glycol monobutyl ether, unsaturated alcohols such as allyl alcohol, 1,1-dimethylallyl alcohol or olein alcohol, aromatic alcohols such as phenol, the isomeric cresols or methoxyphenols, araliphatic alcohols such as benzyl alcohol, anisyl alcohol or cinnamyl alcohol, secondary monoamines such as dimethylamine, diethylamine, dipropylamine, diisopropylamine, dibutylamine, bis(2-ethylhexyl) amine, N-methyl- and N-ethylcyclohexylamine or dicyclohexylamine, and heterocyclic secondary amines such as morpholine, pyrrolidine, piperidine or 1H-pyrazole. Preferred starter molecules are saturated monoalcohols of the abovementioned type. It is particularly preferable to use diethylene glycol monobutyl ether, methanol or n-butanol as starter molecules.

Alkylene oxides suitable for the alkoxylation reaction are especially ethylene oxide and propylene oxide, which can be used in the alkoxylation reaction in any sequence or else in a mixture.

In a preferred embodiment of the invention, the polyurethaneurea used in accordance with the invention contains within a range of ≥0% and ≤20% by weight of component V2D), preferably within a range of ≥0% and ≤10% by weight of component V2D) and most preferably within a range of ≥0% and ≤5% by weight of component V2D), based in each case on the total mass of the polyurethaneurea. In a further preferred embodiment, component V2D) is not used for preparation of the polyurethaneurea.

As component V2E) it is optionally possible to use polyols, especially nonpolymeric polyols, of said molecular weight range from 62 to 399 g/mol having up to 20 carbon atoms, such as ethylene glycol, diethylene glycol, triethylene glycol, propane-1,2-diol, propane-1,3-diol, butane-1,4-diol, 1,3-butylene glycol, cyclohexanediol, cyclohexane-1,4-dimethanol, hexane-1,6-diol, neopentyl glycol, hydroquinone dihydroxyethyl ether, bisphenol A (2,2-bis(4-hydroxyphenyl)propane), hydrogenated bisphenol A (2,2-bis (4-hydroxycyclohexyl)propane), trimethylolpropane, trimethylolethane, glycerol, pentaerythritol and any desired mixtures thereof with one another.

Preferably, the polyurethaneurea used in accordance with the invention contains ≤10% by weight of component V2E), preferably ≤5% by weight and more preferably 0% by weight of component V2E), based in each case on the total mass of the polyurethaneurea. Preferably, the polyurethaneurea includes component V2E) within a range from 0.1% to 10% by weight, preferably within a range from 0.2% to 8% by weight, preferably within a range from 0.1% to 5% by weight, based in each case on the total mass of the polyurethaneurea. In a further preferred embodiment, component V2E) is not used for preparation of the polyurethaneurea.

Preferably, the polyurethaneurea used in accordance with the invention is prepared using within a range of ≥0.5% and ≤20% by weight of the sum total of components C1) and any V2E) and more preferably within a range of ≥1% and ≤15% by weight of the sum total of components C1) and any V2E), based in each case on the total mass of the polyurethaneurea.

As component V2F) it is possible to use further polymeric polyols that are different than V2B).

Examples are polymeric polyols that are not covered by the definition of V2B) and preferably not by the definition of V2E) either because they are not polyether polyols—for example the following polyols that are known per se in polyurethane coating technology: polyester polyols, polyacrylate polyols, polyurethane polyols, polycarbonate polyols, polyester polyacrylate polyols, polyurethane polyacrylate polyols, polyurethane polyester polyols, polyurethane polycarbonate polyols and polyester polycarbonate polyols.

Preferably, component V2F) does not comprise polymeric polyols having ester groups, especially not polyester polyols.

According to the invention, components V2B) and V2F) together contain ≤30% by weight, preferably ≤10% by weight and more preferably ≤5% by weight of component V2F), based on the total mass of components V2B) and V2F). Most preferably, component V2F) is not used for preparation of the polyurethaneurea.

Preferably, the polyurethaneurea used in accordance with the invention is prepared using within a range of ≥55% and ≤90% by weight of the sum total of components V2B) and any V2F) and more preferably within a range of ≥60% and ≤85% by weight of the sum total of components V2B) and any V2F), based in each case on the total mass of the polyurethaneurea.

Component V2G) comprises compounds having exactly one isocyanate-reactive group or compounds having more than one isocyanate-reactive group, where only one of the isocyanate-reactive groups reacts with the isocyanate groups present in the reaction mixture under the reaction conditions chosen.

The isocyanate-reactive groups of component V2G) may be any functional group that can react with an isocyanate group, for example hydroxyl groups, thiol groups or primary and secondary amino groups.

Isocyanate-reactive groups in the context of the invention are especially preferably primary or secondary amino groups that react with isocyanate groups to form urea groups. As well as the amino group, the compounds of component V2G) may also have other groups that are isocyanate-reactive in principle, such as OH groups, where just one of the isocyanate-reactive groups reacts with the isocyanate groups present in the reaction mixture under the reaction conditions chosen. This can be effected, for example, by reaction of appropriate amino alcohols at relatively low temperatures, for example at 0 to 60° C., preferably at 20 to 40° C. Preference is given here to working in the absence of catalysts that would catalyze the reaction of isocyanate groups with alcohol groups.

Examples of suitable compounds of component V2G) are primary/secondary amines, such as methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, diethanolamine, 3-amino-1-methylaminopropane, 3-amino-1-ethylaminopropane, 3-amino-1-cyclohexylaminopropane, 3-amino-1-methylaminobutane, ethanolamine, 3-aminopropanol or neopentanolamine or mixtures of at least two of these.

Suitable monofunctional compounds are also ethanol, n-butanol, ethylene glycol monobutyl ether, diethylene glycol monomethyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethylhexanol, 1-octanol, 1-dodecanol, 1-hexadecanol, and mixtures of at least two of these.

Preferably, the polyurethaneurea used in accordance with the invention is prepared using ≥0.1% and ≤20% by weight of component V2G) and more preferably ≥0.3% and ≤10% by weight of component V2G), based in each case on the total mass of the polyurethaneurea.

Preference is given to using component V2H). Preferably, the molar ratio of component V2G) to component V2H) is 5:1 to 1:5, more preferably 1.5:1 to 1:4 and most preferably 1:1 to 1:3.

Preferably, the polyurethaneureas used in accordance with the invention are prepared using components V2A) to V2H) in the following amounts, where the individual amounts always add up to 100% by weight:
5% to 40% by weight of component V2A),
55% to 90% by weight of the sum total of components V2B) and optionally V2F),
0.5% to 20% by weight of the sum total of components C1) and optionally V2E),
0.1% to 10% by weight of component C2),
0% to 20% by weight of component V2D),
0.1% to 20% by weight of component V2G) and
0% to 10% by weight of component V2H).

Most preferably, the polyurethaneurea used in accordance with the invention is obtainable by reacting exclusively components A) to H). In that case, no further components are used for preparation of the polyurethaneurea.

The number-average molecular weight of the polyurethaneureas used with preference in accordance with the invention is preferably from ≥2000 to ≤300 000 g/mol, preferably from ≥5000 to ≤150 000 g/mol.

The polyurethaneurea used in accordance with the invention is preferably amorphous and has a $T_g$≤−25° C., more preferably of ≤−50° C. and most preferably of ≤−70° C.

"Amorphous" in the context of this invention means that the polyurethaneurea, within the temperature range specified in the test method detailed hereinafter, forms only such minor crystalline components, if any, that, by means of the DSC measurements described, it is possible to find only one or more glass transition points $T_g$ but no fusion regions having an enthalpy of fusion ≥20 J/g within the temperature range mentioned.

The glass transition temperature $T_g$ is determined in the context of this invention by means of dynamic differential calorimetry in accordance with DIN EN 61006, Method A, using a DSC instrument calibrated with indium and lead for determination of $T_g$, by conducting three directly consecutive runs composed of a heating operation from −100° C. to +150° C., at a heating rate of 20 K/min, with subsequent cooling at a cooling rate of 320 K/min, and using the third heating curve to determine the values and determining $T_g$ as the temperature at half the height of a glass transition step.

If the polyurethaneurea should be in the form of a dispersion, a special procedure is followed in the sample preparation for the DSC measurements. In the determination of the glass transition temperature $T_g$ of dispersions by means of DSC, the $T_g$ of the polymer can be masked by the caloric effects of the dispersant (water, neutralizing agent, emulsifier, cosolvent etc.) or distinctly lowered owing to miscibility with the polymer. Therefore, the dispersant, prior to the DSC measurement, is preferably first removed completely by suitable drying, since even small residual amounts of dispersant act as plasticizer and can lower the glass transition temperature as a result. The dispersion is therefore preferably knife-coated onto a glass plate at wet film thickness (WFT) 100 μm, flashed off and then dried gently in a dry box at RT and 0% relative air humidity (rh) for two days. After this sample preparation in the first heating operation of the DSC measurement still a broad endothermic evaporation range of residual moisture in the film can occur. In order to keep the particular values free of such influences as far as possible, the third heating curve is therefore evaluated.

The polyurethaneurea used in accordance with the invention for production of the product is preferably in a physiologically acceptable medium containing isocyanate-reactive groups. The medium is more preferably water, and the polyurethaneurea is most preferably in the form of an aqueous dispersion. In general, alongside other liquid media that are optionally present, for example solvents, water forms the main constituent (≥50% by weight) of the medium, based on the total amount of the liquid medium containing isocyanate-reactive groups, and possibly even the sole liquid medium containing isocyanate-reactive groups.

The viscoelastic element of the invention itself contains the polyurethaneurea per se, which contains only residual amounts of this medium, if any.

Preferably, the polyurethaneurea used is therefore dispersible in water, which means in the context of this invention that the polyurethaneurea at 23° C. can form a sedimentation-stable dispersion in water, especially deionized water.

The polyurethaneureas used in accordance with the invention are preferably obtainable by preparing isocyanate-functional polyurethane prepolymers a) from components V2A), V2B) and optionally V2D) and/or C2), and optionally compounds V2E) and/or V2H) (step a), and the free NCO groups thereof are then wholly or partially reacted with the amino-functional chain-extender component V2C), and also component V2G) and optionally components V2D) and V2H) (step b)).

But when component V2H) is not used until step b), it is preferably added prior to the addition of component V2C) and reacted with the prepolymer a).

In a preferred embodiment of the invention, in step b), reaction is effected with a diamine or multiple diamines (component V2C) with chain extension, also with addition of the monofunctional component V2G) as chain terminator to control the molecular weight.

Components V2A) to V2H) are defined here as specified above. The abovementioned preferred embodiments are also applicable.

Preferably, in step b), the reaction of the prepolymer a) for preparation of the polyurethaneurea, a mixture of components C1), C2) and V2G) is reacted. The use of component C1) can result in formation of a high molar mass without a rise in the viscosity of the isocyanate-functional prepolymer prepared beforehand to a degree that would be a barrier to processing. The use of the combination of components C1), C2) and V2G) can establish an optimal balance between hydrophilicity and chain length.

Preferably, the polyurethane prepolymer a) used in accordance with the invention has terminal isocyanate groups, meaning that the isocyanate groups are at the chain ends of the prepolymer. More preferably, all chain ends of the prepolymer have isocyanate groups.

V2A) to V2H) are defined here as specified above. The abovementioned preferred embodiments are also applicable.

Preferably, in step b), the reaction of the prepolymer a) for preparation of the polyurethaneurea, a mixture of components C1), C2) and V2G) is reacted. The use of component C1) can result in formation of a high molar mass without a rise in the viscosity of the isocyanate-functional prepolymer prepared beforehand to a degree that would be a barrier to processing. The use of the combination of components C1), C2) and V2G) can establish an optimal balance between hydrophilicity and chain length.

Preferably, the polyurethane prepolymer a) used in accordance with the invention has terminal isocyanate groups, meaning that the isocyanate groups are at the chain ends of the prepolymer. More preferably, all chain ends of the prepolymer have isocyanate groups.

The hydrophilizing components C2) and/or V2D) can be used to control the hydrophilicity of the prepolymer. In addition, still further components are of course also significant for the hydrophilicity of the prepolymer, especially also the hydrophilicity of component V2B).

Preferably, the isocyanate-functional polyurethane prepolymers a) are water-insoluble and non-water-dispersible.

In the context of the invention, the term "water-insoluble, non-water-dispersible polyurethane prepolymer" means more particularly that the water solubility of the prepolymer used in accordance with the invention at 23° C. is less than 10 g/liter, preferably less than 5 g/liter, and the prepolymer at 23° does not result in any sedimentation-stable dispersion in water, especially deionized water. In other words, the prepolymer settles out when an attempt is made to disperse it in water. The water insolubility or lack of dispersibility in water relates to deionized water without addition of surfactants.

Moreover, the polyurethane prepolymer a) used in accordance with the invention preferably has essentially neither ionic groups nor ionogenic groups (groups capable of forming ionic groups). In the context of the present invention, this means that the proportion of the ionic and/or ionogenic groups, such as anionic groups in particular, such as carboxylate or sulfate, or of cationic groups is less than 15 milliequivalents per 100 g of polyurethane prepolymer a1), preferably less than 5 milliequivalents, more preferably less than 1 milliequivalent and most preferably less than 0.1 milliequivalent per 100 g of polyurethane prepolymer a).

In the case of acidic ionic and/or ionogenic groups, the acid number of the prepolymer is appropriately below 30 mg KOH/g of prepolymer, preferably below 10 mg KOH/g of prepolymer. The acid number indicates the mass of potassium hydroxide in milligrams required to neutralize 1 g of the sample to be examined (measurement to DIN EN ISO 211). The neutralized acids, i.e. the corresponding salts, naturally have a zero or reduced acid number. What is crucial here in accordance with the invention is the acid number of the corresponding free acid.

The water-insoluble, non-water-dispersible isocyanate-functional polyurethane prepolymers a) here are preferably obtainable exclusively from components V2A), V2B) and optionally V2D), V2E) and/or V2H).

The components are defined here as specified above. The abovementioned preferred embodiments are also applicable.

Consequently, in this embodiment, preference is given to using no ionically hydrophilizing components C2) or else D2) for preparation of the prepolymer a). Nor is component V2G) added in this step. The hydrophilizing agents D1) are preferably used in such amounts that the prepolymer is nevertheless water-insoluble and non-water-dispersible. More preferably ≤10% by weight of component D1), even more preferably ≤5% by weight and further preferably ≤2% by weight of component D1) is used, based in each case on the total mass of the polyurethaneurea. Further preferably, component D1) is not used for preparation of the prepolymer a).

For this embodiment of the invention, component V2B) has neither ionic nor ionogenic groups. In addition, in this embodiment of the invention, preference is given to using, as component V2B), polyether polyols only, especially polyalkylene oxide ethers containing ≤10 mol % and, based on all alkylene oxide units present, of ethylene oxide units and preferably no ethylene oxide units.

The polyurethaneureas used with preference in this embodiment of the invention consequently have ionic or ionogenic groups, preferably anionic groups; these anionic groups are introduced into the polyurethaneureas used in accordance with the invention via the hydrophilizing component C2) used in step b). The polyurethaneureas used in accordance with the invention optionally additionally include nonionic components for hydrophilization.

More preferably, the polyurethaneureas used in accordance with the invention, for hydrophilization, contain exclusively sulfonate groups that are introduced into the polyurethaneurea in step b) via corresponding diamines as component C2).

In an alternative, less preferred embodiment of the invention, the prepolymers a) used for preparation of the polyurethaneurea of the invention are water-soluble or water-dispersible. In this embodiment, the hydrophilizing components V2D) and/or C2) are used in the preparation of the prepolymer a) in an amount sufficient for the prepolymer to be water-soluble or water-dispersible. The prepolymer a) here preferably has ionic or ionogenic groups.

Suitable hydrophilizing components V2D) and C2) for this embodiment of the invention are the compounds mentioned above for V2D) and C2). The hydrophilizing components used are preferably at least the compounds mentioned above under D1) and/or C2).

The polyurethaneureas used for preparation of the products of the invention are preferably dispersed in water before, during or after step b), more preferably during or after step b). In this way, a dispersion of the polyurethaneureas is obtained.

The production of the polyurethaneurea dispersions can be conducted here in one or more stage(s) in a homogeneous reaction or in a multistage reaction, partly in disperse phase. Preparation of the prepolymer a) is preferably followed by a dispersion, emulsification or dissolution step. This is optionally followed by a further polyaddition or modification in disperse phase. In this case, the solvent or dispersant suitable for the corresponding prepolymer in each case, for example water or acetone or mixtures thereof, is chosen.

It is possible here to use any methods known from the prior art, for example prepolymer mixing methods, acetone methods or melt dispersion methods. Preference is given to employing the acetone method.

For preparation by the acetone method, it is customary to wholly or partly initially charge constituents V2B), optionally V2D) and V2E) and the polyisocyanate component V2A), optionally in combination with component V2H) for preparation of an isocyanate-functional polyurethane prepolymer, and optionally to dilute them with a solvent which is water-miscible but inert toward isocyanate groups, and to heat them to temperatures in the range from 50 to 120° C. The isocyanate addition reaction can be accelerated using the catalysts known in polyurethane chemistry.

Suitable solvents are the customary aliphatic keto-functional solvents, such as acetone, 2-butanone, which can be added not just at the start of the preparation but optionally also in portions at a later stage. Acetone and 2-butanone are preferred and acetone is particularly preferred. The addition of other solvents without isocyanate-reactive groups is also possible, but not preferred.

Subsequently, any constituents of V2A), V2B) and optionally V2H), V2D) and V2E) which have not yet been added at the start of the reaction can be metered in.

In the preparation of the polyurethane prepolymer from V2A), V2B) and optionally V2H), V2D) and V2E), the molar ratio of isocyanate groups to isocyanate-reactive groups is preferably 1.05 to 3.5, more preferably 1.1 to 3.0 and most preferably 1.1 to 2.5.

The conversion of components V2A), V2B) and optionally V2H), V2D) and V2E) to the prepolymer can be effected in part or in full, but preferably in full. In this way, polyurethane prepolymers containing free isocyanate groups can be obtained in neat form or in solution.

If ionogenic groups, for example carboxyl groups, should be present in the prepolymer, these can be converted to ionic groups by neutralization in a further step.

In the neutralization step, for partial or complete conversion of potentially anionic groups to anionic groups, it is possible to use bases such as tertiary amines, e.g. trialkylamines having 1 to 12 and preferably 1 to 6 carbon atoms, more preferably 2 to 3 carbon atoms, in each alkyl radical, or most preferably alkali metal bases such as the corresponding hydroxides.

Usable neutralizing agents are preferably inorganic bases, such as aqueous ammonia solution or sodium hydroxide or potassium hydroxide; particular preference is given to sodium hydroxide and potassium hydroxide.

The molar amount of the bases is preferably 50 and 125 mol %, more preferably between 70 and 100 mol %, of the molar amount of the acid groups to be neutralized. Neutralization can also be effected simultaneously with the dispersion, in that the dispersion water already contains the neutralizing agent.

After the neutralization, in a further process step, if this has been done only partly, if at all, the prepolymer obtained is dissolved with the aid of aliphatic ketones such as acetone or 2-butanone.

In the chain extension/termination in stage b), components V2C), V2G) and optionally V2D) are reacted with the isocyanate groups still remaining in the prepolymer. It is preferable when the chain extension/termination is carried out prior to the dispersing in water.

Suitable components V2C) for chain extension and V2G) for chain termination have already been listed above. The abovementioned preferred embodiments are also applicable analogously.

If anionic hydrophilizing agents in accordance with definition C2) having NH2 groups or NH groups are used for chain extension, the chain extension of the prepolymers in step b) is preferably effected prior to the dispersion in water.

The equivalent ratio of NCO-reactive groups in the compounds used for chain extension and chain termination to free NCO groups in the prepolymer is generally between 40% and 150%, preferably between 50% and 110%, more preferably between 60% and 100%.

Components C1), C2) and V2G) may optionally be used in water- or solvent-diluted form in the process of the invention, individually or in mixtures, any sequence of addition being possible in principle.

When water or organic solvents are included as diluent in step b), the respective diluent content in components C1), C2) and V2G) used is preferably 40% to 95% by weight.

Dispersion preferably follows after the chain extension and chain termination. For this purpose, the polyurethane polymer that has been dissolved (for example in acetone) and reacted with the amine is either introduced into the dispersion water, optionally under high shear, for example vigorous stirring, or, conversely, the dispersion water is stirred into the chain-extended polyurethane polymer solutions. Preferably, the water is added to the dissolved polyurethane polymer.

The solvent still present in the dispersions after the dispersion step is typically then removed by distillation. Removal even during the dispersion is likewise possible.

The aqueous polyurethaneurea dispersions obtained preferably have a content of volatile organic compounds (VOCs), for example volatile organic solvents, of less than 10% by weight, more preferably of less than 3% by weight, even more preferably of less than 1% by weight, based on the aqueous polyurethaneurea dispersion. VOCs in the context of this invention are especially organic compounds having an initial boiling point of at most 250° C. at a standard pressure of 101.3 kPa.

In the context of the present invention, the content of volatile organic compounds (VOCs) is especially determined by gas chromatography analysis.

The polyurethaneurea is used for preparation of the product preferably as an aqueous dispersion.

The pH of the aqueous polyurethane dispersions used in accordance with the invention is typically less than 9.0, preferably less than 8.5, and is more preferably between 5.5 and 8.0.

In order to achieve good sedimentation stability, the number-average particle size of the specific polyurethaneurea dispersions is preferably less than 750 nm, more preferably less than 500 nm, determined by means of laser correlation spectroscopy after dilution with deionized water (instrument: Malvern Zetasizer 1000, Malvern Inst. Limited).

The solids content of the polyurethaneurea dispersions is preferably 10% to 70% by weight, more preferably 20% to 60% by weight and most preferably 40% to 60% by weight. The solids contents are ascertained by heating a weighed sample to 125° C. to constant weight. At constant weight, the solids content is calculated by reweighing the sample.

Preferably, these polyurethaneurea dispersions include less than 5% by weight, more preferably less than 0.2% by weight, based on the mass of the dispersions, of unbound organic amines The polyurethaneurea dispersions used for production of the products of the invention have, at 23° C., at a constant shear rate of 10 s$^{-1}$, preferably a viscosity of ≥1 and ≤10 000 mPa s, more preferably of ≥10 and ≤5000 mPa s and most preferably of ≥100 and ≤4000 mPa s. The viscosity is determined as described in the Methods section.

In a preferred embodiment of the viscoelastic element, the components (V1) with (V2) lie in the reaction of the components (V1) and (V2) in a weight ratio of 5:1 to 1:1, or preferably of 4:1 to 1:1, or preferably of 3:1 to 1:1, based on the total weight of the two components (V1) and (V2).

In a preferred embodiment of the viscoelastic element, the viscoelastic element has at least one of the following properties:
i. damping (from compression hardness measurement) of 0.40 to 0.90, or preferably of 0.45 to 0.80, or preferably of 0.45 to 0.70, measured to DIN EN ISO 3386-1:2015-10;
ii. breaking stress within a range from 0.12 MPa to 0.40 MPa, or preferably from 0.13 to 0.35 MPa, or preferably from 0.14 to 0.30 MPa, or preferably from 0.15 to 0.25 MPa, measured to DIN EN ISO 527-2;
iii. elongation at break within a range from 150% to 300%, or preferably from 180% to 290%, or preferably from 200% to 280%, or preferably from 220% to 270%, measured to DIN EN ISO 527-2;
iv. water absorption of ≤1800% (g/g), or preferably of ≤1700% (g/g), or preferably of ≤1500% (g/), based on weight of the dry foam, measured to DIN EN 13726-1;
v. retention of ≤80%, or preferably of ≤70%, or preferably of ≤60%, or preferably within a range of ≥20% to ≤80%, or preferably within a range of ≥30% to ≤70%, based on the maximum absorption, as described later under Methods;
vi. recovery time after compression of the original volume by 50% (at a pressure of 7 kPa) to at least 90% of the original volume at standard pressure and RT within a range from 2 to 50 seconds, or preferably from 3 to 40, or preferably from 4 to 30;
vii. volume within a range from 0.1 cm$^3$ to 1 m$^3$, or preferably from 0.15 cm$^3$ to 0.5 m$^3$, or preferably from 0.2 cm$^3$ to 0.1 m$^3$;
viii. density within a range from 150 to 400 g/l, or preferably from 170 to 380 g/l, or preferably from 180 to 350 g/l, or preferably from 200 to 300 g/l;
ix. loss factor ≥0.140 (from rheological studies), preferably a loss factor within a range from 0.140 to 0.400, or preferably from 0.150 to 0.350, or preferably from 0.160 to 0.300, measured to DIN EN ISO 6721-1;
x. modulus of elasticity to DIN EN ISO 527-2 within a range from 0.08 MPa to 0.25 MPa, or preferably from 0.08 MPa to 0.2 MPa, or preferably from 0.08 MPa to 0.15 MPa.

The viscoelastic element may have all possible combinations of features i. to x. Preferably, the viscoelastic element has at least feature vi., and further preferably the combination of features of vi. and at least one of features i., ii. or iii. Preferably, the viscoelastic element has the combination of features i. to iii. and vi. Further preferably, the viscoelastic element has the combination of features i. to vi. Preferably, the viscoelastic element has all of features i. to x.

In a preferred embodiment of the viscoelastic element, components V2B) and V2F) together contain ≤30% by weight of component V2F), based on the total mass of components V2B) and V2F).

In a preferred embodiment of the viscoelastic element, component V2A) is isophorone diisocyanate and/or hexamethylene diisocyanate. Preferably, component V2A) comprises exclusively isophorone diisocyanate and/or hexamethylene diisocyanate.

In a preferred embodiment of the viscoelastic element, component V2B) contains or consists of poly(tetramethylene glycol) polyether polyols (such as (HO—(CH$_2$—CH$_2$—CH$_2$—CH$_2$—O)$_x$—H). Preferably, component V2B) contains the poly(tetramethylene glycol) polyether polyols to an extent of at least 50% by weight, or preferably to an extent of at least 70% by weight, or preferably to an extent of at least 90% by weight, based on the total mass of component V2B).

In a preferred embodiment of the viscoelastic element, component (V1) is an isocyanate-functional prepolymer having a proportion by weight of low molecular weight, aliphatic diisocyanates having a molar mass of ≥140 to ≤278 g/mol, preferably ≥168 to ≤258 g/mol, of ≤1.0% by weight, based on the prepolymer, obtainable by reaction of V1A) low molecular weight, or aliphatic diisocyanates of molar mass from ≥140 to ≤278 g/mol or preferably ≥168 to ≤258 g/mol, with V1B) di- to hexafunctional polyalkylene oxides of OH number from ≥22.5 to ≤112 mg KOH/g and of ethylene oxide content from ≥50 to ≤100 mol %, based on the total amount of oxyalkylene groups present, V1C) optionally heterocyclic 4-membered or 6-membered ring oligomers of low molecular weight, or aliphatic diisocyanates having a molar mass of ≥140 to ≤278 g/mol, or preferably ≥168 to ≤258 g/mol, V1D) optionally catalysts, V1E) optionally alkali metal salts of weak inorganic acids, V1F) optionally surfactants, V1G) optionally mono- or polyhydric alcohols, V1H) the following components:
V1H1) one or more low molecular weight, aliphatic diisocyanates having a molar mass of ≥140 to ≤278 g/mol, preferably ≥168 to ≤258 g/mol and/or polyisocyanates preparable therefrom that have an isocyanate functionality of ≥2 to ≤6;

and/or

V1H2) one or more monofunctional polyalkylene oxides having an OH number of ≥10 to ≤250 and an ethylene oxide content of ≥50 to ≤100 mol %, based on the total amount of oxyalkylene groups present;

and/or

V1H3) a hydrophilic isocyanate component obtainable by the reaction of components mentioned under V1H1) with components mentioned under V1H2).

The hydrophilic polyisocyanates mentioned under V1H) are typically prepared by reaction of 1 mol of OH groups of the monofunctional polyalkylene oxide component V1H2) with 1.25 to 15 mol, preferably with 2 to 10 mol and more preferably 2 to 6 mol of NCO groups of a polyisocyanate V1H1) having an isocyanate functionality of 2 to 6, based on aliphatic diisocyanates. Examples of such polyisocyanates V1H1) are biuret structures, isocyanurates or uretdiones based on aliphatic diisocyanates. The polyisocyanate V1H1) and the polyalkylene oxide V1H2) are preferably joined to one another via a urethane group or a urea group, preference being given particularly to linkage via urethane groups.

The NCO content of the isocyanate-functional prepolymers V1A) is preferably 1.5% to 4.5% by weight, more preferably 1.5% to 3.5% by weight and most preferably 1.5% to 3.0% by weight.

Examples of low molecular weight, aliphatic diisocyanates of component V1A) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, preference being given to hexamethylene diisocyanate (HDI), isophorone diisocyanate (IPDI), butylene diisocyanate (BDI), and bis(isocyanatocyclohexyl)methane (HMDI). Particular preference is given to BDI, HDI, IPDI, very particular preference to hexamethylene diisocyanate and isophorone diisocyanate.

Urea/urethane formation can be accelerated by using catalysts in component V1D). These are typically the compounds known to the person skilled in the art from polyurethane technology. Preference is given here to compounds from the group consisting of catalytically active metal salts, amines, amidines and guanidines. Examples include dibutyltin dilaurate (DBTL), tin acetate, 1,8-diazabicyclo[5.4.0]undecene-7 (DBU), 1,5-diazabicyclo[4.3.0]nonene-5 (DBN), 1,4-diazabicyclo[3.3.0]octene-4 (DBO), N-ethylmorpholine (NEM), triethylenediamine (DABCO), pentamethylguanidine (PMG), tetramethylguanidine (TMG), cyclotetramethylguanidine (TMGC), n-decyltetramethylguanidine (TMGD), n-dodecyltetramethylguanidine (TMGDO), dimethylaminoethyltetramethylguanidine (TMGN), 1,1,4,4,5,5-hexamethylisobiguanidine (HMIB), phenyltetramethylguanidine (TMGP) and hexamethyleneoctamethylbiguanidine (HOBG).

Preference is given to the use of amines, amidines, guanidines or mixtures thereof as catalysts of component V1D). Preference is also given to the use of 1,8-diazabicyclo[5.4.0]undecene-7 (DBU).

But it is also possible to dispense with catalysts; this is preferred.

Alkali metal salts of weak inorganic acids are used as component V1E). These are understood to mean alkali metal salts of inorganic acids, the corresponding free acids of which have a pKa in water at 25° C. of >4.0. Examples of particularly suitable alkali metal salts of weak inorganic acids are potassium hydroxide, sodium hydroxide, potassium carbonate, sodium carbonate and sodium hydrogencarbonate, including any mixtures of these salts.

Foam formation, foam stability or the properties of the resulting polyurethane foam may be improved by using compounds of component V1F), where such additives may in principle be any of the anionic, cationic, amphoteric and nonionic surfactants that are known per se, and mixtures of these. Preference is given to using alkyl polyglycosides, EO/PO block copolymers, alkyl or aryl alkoxylates, siloxane alkoxylates, esters of sulfosuccinic acid and/or alkali metal or alkaline earth metal alkanoates. Particular preference is given to using EO/PO block copolymers. Preference is given to using solely the EO/PO block copolymers as component V1F).

In addition, the foam properties of the resulting polyurethane foam can be improved by using compounds of component V1G). These are in principle all the mono- and polyhydric alcohols that are known per se to the person skilled in the art, and mixtures of these. These are mono- or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyetherdiols and polyesterdiols.

In the preparation of the hydrophilic polyisocyanates listed under V1H), the ratio of the monofunctional polyalkylene oxides V1H2) to the low molecular weight, aliphatic diisocyanates V1H1) is preferably adjusted such that, for every 1 mol of OH groups of the monofunctional polyalkylene oxides, there are 1.25 to 15 mol, preferably 2 to 10 mol and more preferably 2 to 6 mol of NCO groups of the low molecular weight, aliphatic diisocyanate V1H1). This is followed by allophanatization or biuretization and/or isocyanurate formation or uretdione formation. If the polyalkylene oxides V1H2) are bonded to the aliphatic diisocyanates V1H1) via urethane groups, allophanatization preferably takes place thereafter. It is further preferable that isocyanurate structural units are formed.

The reaction can be effected in the presence of urethanization catalysts such as tin compounds, zinc compounds, amines, guanidines or amidines, or in the presence of allophanatization catalysts such as zinc compounds.

The reaction is typically effected at 25° C. to 140° C., preferably 60° C. to 100° C.

Examples of low molecular weight, aliphatic diisocyanates of component V1H1) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, preference being given to hexamethylene diisocyanate (HDI), isophorone diisocyanate (IPDI), butylene diisocyanate (BDI), and bis(isocyanatocyclohexyl)methane (HMDI). Particular preference is given to BDI, HDI, IPDI, very particular preference to hexamethylene diisocyanate and isophorone diisocyanate. Examples of higher molecular weight polyisocyanates V1H2) are polyisocyanates having an isocyanate functionality of 2 to 6 with isocyanurate, urethane, allophanate, biuret, iminooxadiazinetrione, oxadiazinetrione and/or uretdione groups, based on the aliphatic and/or cycloaliphatic diisocyanates mentioned in the paragraph above.

Components V1H1) used are preferably higher molecular weight compounds with biuret, iminooxadiazinedione, isocyanurate and/or uretdione groups, based on hexamethylene diisocyanate, isophorone diisocyanate and/or 4,4'-diisocyanatodicyclohexylmethane. Preference is further given to isocyanurates. Very particular preference is given to structures based on hexamethylene diisocyanate.

The monofunctional polyalkylene oxides V1H2) have an OH number of 15 to 250, preferably of 28 to 112, and an ethylene oxide content of 50 to 100 mol %, preferably of 60 to 100 mol %, based on the total amount of the oxyalkylene groups present.

Monofunctional polyalkylene oxides in the context of the invention are understood to mean compounds that have only one isocyanate-reactive group, i.e. one group that can react with an NCO group.

The preparation of polyalkylene oxides V1H2) by alkoxylation of suitable starter molecules is known from the literature (e.g. Ullmanns Enzyklopadie der technischen Chemie [Ullmann's Encyclopedia of Industrial Chemistry], 4th edition, volume 19, Verlag Chemie, Weinheim p. 31-38). Suitable starter molecules are especially saturated monoalcohols such as methanol, ethanol, n-propanol, isopropanol, n-butanol, isobutanol, sec-butanol, diethylene glycol monobutyl ether, and aromatic alcohols such as phenol or monoamines such as diethylamine Preferred starter molecules are saturated monoalcohols of the abovementioned type. It is particularly preferable to use diethylene glycol monobutyl ethers or n-butanol as starter molecules. The monofunctional polyalkylene oxides V1H2) typically have number-average molecular weights of 220 to 3700 g/mol, preferably of 500 to 2800 g/mol.

The monofunctional polyalkylene oxides V1H2) preferably have an OH group as isocyanate-reactive group.

The invention further relates to a process for producing a viscoelastic element, comprising the steps of:
I) mixing an isocyanate-functional polyurethane prepolymer (V1) with at least one polyurethaneurea dispersion (V2) in the presence of a medium containing isocyanate-reactive groups to obtain a polyurethane prepolymer/medium mixture, the medium preferably being water,
II) applying the polyurethane prepolymer/medium mixture from step I) to a substrate;
III) curing the polyurethane prepolymer/medium mixture, where the medium is preferably water and the polyurethane prepolymer/medium mixture is especially a polyurethane prepolymer/water mixture, from step II) to obtain the viscoelastic element;
IV) optionally removing the viscoelastic element from the substrate.

In a preferred embodiment of the process, the mixing in step I) is effected within 3 to 90, preferably within 5 to 60, or preferably within 6 to 30 seconds before the mixture is applied to the substrate in step II).

The mixing in step I) can be effected by means of any mixing method that would be selected for the purpose by the person skilled in the art. The mixing is preferably effected by means of a disk stirrer, Speedmixer, anchor stirrer, precision glass stirrer, a static, dynamic or static-dynamic stirrer, or a low-pressure two-component mixing unit. The mixing in step I) preferably takes place at a temperature within a range from 10 to 100° C., or preferably within a range from 20 to 60° C., or preferably within a range from 23 to 50° C. The mixing in step I) preferably takes place within a pressure range from atmospheric pressure to a pressure of 20 bar. The mixing preferably takes place at standard pressure.

The application of the polyurethane prepolymer/medium mixture from step I) to a substrate in step II) can be effected in any way that would be selected for the purpose by the person skilled in the art. The mode of application is preferably selected from the group consisting of pouring, spraying, printing or a combination of at least two of these. That pouring can be effected from any vessel that would be used for the purpose by the person skilled in the art. The spraying can be effected by means of any spraying tool that would be used for the purpose by the person skilled in the art. The spraying preferably takes place by means of a nozzle having a diameter within a range from 0.1 mm to 10 m, or preferably within a range from 0.5 mm to 1 m, or preferably within a range from 1 mm to 50 cm. The substrate may be any substrate that would be selected for the purpose by the person skilled in the art. The substrate is preferably made from a material that does not enter into any reaction with the polyurethane prepolymer/medium mixture, especially the polyurethane prepolymer/water mixture, from step II). The substrate is preferably selected such that it can easily be detached from the cured viscoelastic element without the element incurring damage or leaving residues of the element on the substrate. The substrate is preferably selected from the group consisting of a polymer, a glass, a ceramic, a paper, a coated paper, a wood, a metal or a combination of these.

The curing of the polyurethane prepolymer/medium mixture, especially of the polyurethane prepolymer/water mixture, from step II) in step III) to obtain the viscoelastic element can be effected under any condition that would be chosen for the purpose by the person skilled in the art. The curing preferably takes place at a temperature within a range from 20 to 100° C., or preferably within a range from 30 to 80° C., or preferably within a range from 40 to 70° C. The curing preferably takes place over a period within a range from 1 to 180 minutes, or preferably within a range from 2 to 100 minutes, or preferably within a range from 5 to 60 minutes, or preferably within a range from 7 to 30 minutes. The curing preferably takes place at a temperature within a range from 40 to 80° C. for a period of 2 to 30 minutes. The temperature is preferably controlled by means of a hot air oven, a hot air gun, a heated substrate, a radiator, for example an IR radiator, or a combination of these.

The medium is more preferably water. Alongside other liquid media that are optionally present, for example solvents, water generally forms the main constituent (≥50% by weight) of the medium, based on the total amount of the polyurethane prepolymer/medium mixture, and optionally even the sole medium present in liquid form.

The invention further relates to an earplug for introduction into an ear or an auditory canal, including a viscoelastic element of the invention or a viscoelastic element that has been produced by the process of the invention.

The invention further relates to the use of the above-described viscoelastic element of the invention and of the viscoelastic element produced by the process of the invention for minimization of noise in an interior. An interior may be understood here to mean any volume surrounded by at least one wall. A suitable interior is any volume that would be selected for the purpose by the person skilled in the art. Examples of an interior are at least part of a car interior, at least part of an aircraft interior, an auditory canal or an interior of the ear, a bed or bed frame, a chair or chair frame, a cushion or cushion cover, or a combination of at least two of these.

Preference is given to the use of the above-described viscoelastic element of the invention and of the viscoelastic element produced by the process of the invention for reduction of pressure points on parts of the body. Examples of these are viscoelastic elements in the form of mattresses, pillows, chair cushions, armchair cushions, car seats, aircraft seats or combinations of at least two of these that can preferably be used for the purpose of supporting at least one part of the body over a period of several hours, or preferably of several days, or preferably of several weeks, without evolution of pressure points on the parts of the body supported.

The invention further relates to a kit for producing a viscoelastic element, consisting of
- (V1) an isocyanate-functional polyurethane prepolymer;
- (V2) a polyurethaneurea dispersion.

All remarks that have been made above for components (V1) and (V2) in association with the viscoelastic element of the invention are likewise applicable to components (V1) and (V2) of the kit.

In a preferred embodiment of the kit, component (V2) is in the form of an aqueous dispersion. What is meant by an aqueous dispersion has already been described for the viscoelastic element of the invention and is likewise applicable to the kit.

In a preferred embodiment of the kit, component (V1) is obtainable by reaction of at least the following components:
- V1A) aliphatic diisocyanates with
- V1B) di- to hexafunctional polyalkylene oxides having an ethylene oxide content of 50 to 100 mol %, based on the total amount of oxyalkylene groups present.

In a preferred embodiment of the kit, the polyurethaneurea of the polyurethaneurea dispersion V2) is obtainable by reacting at least
- V2A) an aliphatic polyisocyanate component having an average isocyanate functionality of ≥1.8 and ≤2.6,
- V2B) a polymeric polyether polyol component,
- V2C) an amino-functional chain extender component having at least 2 isocyanate-reactive amino groups, containing at least one amino-functional compound C1) that does not have any ionic or ionogenic groups and/or an amino-functional compound C2) that has ionic or ionogenic groups,
- V2D) optionally further hydrophilizing components different than C2) or
- V2E) optionally hydroxy-functional compounds having a molecular weight of 62 to 399 g/mol or
- V2F) optionally at least one further polymeric polyol different than V2B) or
- V2G) a compound having exactly one isocyanate-reactive group or a compound having more than one isocyanate-reactive group, where only one of the isocyanate-reactive groups reacts with the isocyanate groups present in the reaction mixture under the reaction conditions chosen, and optionally an aliphatic polyisocyanate component having an average isocyanate functionality of ≥2.6 and ≤4.

Methods:

Unless indicated otherwise, all percentages are based on the total weight of the compositions.

Unless noted otherwise, all analytical measurements relate to measurements at temperatures of 23° C. (also referred to as room temperature RT) and standard pressure.

Thickness Measurement:

The determination of layer thickness was ascertained with a compressed air gauge connected to a display from Heidehain (MT25P) to display the layer thickness.

Density Measurement:

To determine the density, a piece of sample was punched out with the aid of a punch in dimensions of 5×5 $cm^2$ (with rounded corners and a curve radius of 3 mm). The height was ascertained from the average of a 5-fold determination by means of the method described above. For subsequent calculation of the density, the mass of the piece of sample was determined using a Mettler Toledo XS603S balance.

Retention:

The maximum absorption of the foam was determined to DIN EN 13726-1:2002-06 on a piece of foam of size 5×5 cm. The piece of foam of size 5×5 cm, after complete absorption of the test solution A (prepared according to DIN EN 13726-1:2002-06) is picked up with tweezers and allowed to drip for 30 seconds and weighed.

The piece of foam is placed on a metal platform and subjected uniformly to a weight of 6 kg for 20 seconds. The weight is removed and, after removing the weight, the piece of foam is weighed again. The remaining amount of moisture is determined by comparison as a percentage of the maximum absorption.

Determination of Recovery Time:

A cylindrical piece of foam of dimensions 6 cm×7 cm (diameter×height) was subjected to a weight of 2 kg (corresponding to a pressure of 7 kPa). After compression to about 50% and subsequent removal of the weight, the time taken for the foam cylinder to reach at least 90% of its original height again was ascertained.

Production of a Viscoelastic Foam of the Invention:

EXAMPLE 1 (B1): ADHESIVE-FREE WOUND CONTACT FOAM 125 g of Baymedix® FP505 (V1), available from Covestro Germany AG, was mixed with 75 g of an aqueous solution of 0.44% by weight of sodium hydrogencarbonate (available from Fluka, Germany), 1.6% by weight of Pluronic® PE6800 (available from BASF SE, Germany), 0.13% by weight of citric acid monohydrate (available from ACROS Organics) and 66.6% by weight of Baymedix® AD111 (V2) (available from Covestro) with vigorous stirring for 7 s with the aid of a stirrer system having an anchor stirrer blade (Labordissolver 5 green 037 from Pendraulik GmbH) at 930 rpm and then applied in x-y direction to a release paper of the Y 05200 type from Felix Schöller Group, Osnabrück, using a squeegee with a 1.5 mm gap. Thereafter, the surface of the reaction mixture extending in x-y direction was covered with a needled variant (including holes having a diameter of 0.1 $mm^2$ and a hole density of 10 per $cm^2$) of the same paper.

The following measurement results were ascertained:

| Test method: | Unit | Result: |
|---|---|---|
| Density | g/l | 277 |
| Absorption | % | 1080 |
| Retention | % | 55 |
| Breaking stress | MPa | 0.19 |
| Elongation at break | % | 255 |
| Modulus of elasticity | MPa | 0.094 |
| Recovery time | s | 13 |

| Test method: | Unit | Result: |
|---|---|---|
| Loss factor (tan δ) at 1 Hz | — | 0.286 |
| Damping (from compression hardness) | — | 0.52 |

EXAMPLE 2 (B2) ADHESIVE-FREE WOUND CONTACT FOAM 125 g of Baymedix® FP505 (V1), available from Covestro Germany AG, was mixed with 50 g of an aqueous solution of 0.66% by weight of sodium hydrogencarbonate (available from Fluka, Germany), 2.4% by weight of Pluronic® PE6800 (available from BASF SE, Germany), 0.2% by weight of citric acid monohydrate (available from ACROS Organics) and 50.0% by weight of Baymedix® AD111 (V2) (available from Covestro) with vigorous stirring for 7 s with the aid of a stirrer system having an anchor stirrer blade (Labordissolver 5 green 037 from Pendraulik GmbH) at 930 rpm and then applied in x-y direction to a release paper of the Y 05200 type from Felix Schöller Group, Osnabrück, using a squeegee with a 1.5 mm gap. Thereafter, the surface of the reaction mixture extending in x-y direction was covered with a needled variant (including holes having a diameter of 0.1 mm$^2$ and a hole density of 10 per cm$^2$) of the same paper.

The following measurement results were ascertained:

| Test method: | Unit | Result: |
|---|---|---|
| Density | g/l | 210 |
| Absorption | % | 1409 |
| Retention | % | 46 |
| Breaking stress | MPa | 220 |
| Elongation at break | % | 0.14 |
| Modulus of elasticity | MPa | 0.096 |
| Recovery time | s | 4 |
| Loss factor (tan δ) at 1 Hz | — | 0.187 |
| Damping (from compression hardness) | — | 0.47 |

COMPARATIVE EXAMPLE (VB1) (NOT ACCORDING TO THE INVENTION)

125 g of Baymedix® FP505 (V1), available from Covestro Germany AG, was mixed with 25 g of an aqueous solution of 1.32% by weight of sodium hydrogencarbonate (available from Fluka, Germany), 4.8% by weight of Pluronic® PE6800 (available from BASF SE, Germany), 0.4% by weight of citric acid monohydrate (available from ACROS Organics, Belgium) with vigorous stirring for 7 s with the aid of a stirrer system having an anchor stirrer blade (Labordissolver 5 green 037 from Pendraulik GmbH) at 930 rpm and then applied in x-y direction to a release paper of the Y 05200 type from Felix Schöller Group, Osnabrück, using a squeegee with a 1.5 mm gap. Thereafter, the surface of the reaction mixture extending in x-y direction was covered with a needled variant (including holes having a diameter of 0.1 mm$^2$ and a hole density of 10 per cm$^2$) of the same paper.

| Test method: | Unit | Result: |
|---|---|---|
| Density | g/l | 133 |
| Absorption | % | 1874 |

| Test method: | Unit | Result: |
|---|---|---|
| Retention | % | 71 |
| Breaking stress | MPa | 0.09 |
| Elongation at break | % | 129 |
| Modulus of elasticity | MPa | 0.078 |
| Recovery time | s | 1 |
| Loss factor (tan δ) at 1 Hz | — | 0.137 |
| Damping (from compression hardness) | — | 0.35 |

COMPARATIVE EXAMPLE (VB2) (NOT ACCORDING TO THE INVENTION)

125 g of prepolymer mixture from patent BMS111012 (Example 1) was mixed with 22.5 g of an aqueous solution of 2.6% by weight of sodium oleate (available from abcr GmbH, Germany), and 55.6% by weight of Baymedix® FD10, available from Covestro Deutschland AG, with vigorous stirring for 7 s with the aid of a stirrer system having an anchor stirrer blade (Labordissolver 5 green 037 from Pendraulik GmbH) at 930 rpm and then applied in x-y direction to a release paper of the Y 05200 type from Felix Schöller Group, Osnabrück, using a squeegee with a 1.5 mm gap. Thereafter, the surface of the reaction mixture extending in x-y direction was covered with a needled variant as described in (B1) of the same paper.

| Test method: | Unit | Result: |
|---|---|---|
| Density | g/l | not determined (n.d.) |
| Absorption | % | n.d. |
| Retention | % | n.d. |
| Breaking stress | MPa | n.d. |
| Elongation at break | % | n.d. |
| Modulus of elasticity | MPa | n.d. |
| Recovery time | s | 1 |
| Loss factor (tan δ) at 1 Hz | — | n.d. |
| Damping (from compression hardness) | — | 0.26 |

COMPARATIVE EXAMPLE (VB3) (NOT ACCORDING TO THE INVENTION)

125 g of prepolymer mixture from patent BMS111012 (Example 2) was mixed with 55.8 g of an aqueous solution of 1.1% by weight of sodium oleate (available from abcr GmbH, Germany), and 78.5% by weight of Baymedix® FD103, available from Covestro Deutschland AG, with vigorous stirring for 7 s with the aid of a stirrer system having an anchor stirrer blade (Labordissolver 5 green 037 from Pendraulik GmbH) at 930 rpm and then applied in x-y direction to a release paper of the Y 05200 type from Felix Schöller Group, Osnabrück, using a squeegee with a 1.5 mm gap. Thereafter, the surface of the reaction mixture extending in x-y direction was covered with a needled variant as described in (B1) of the same paper.

| Test method: | Unit | Result: |
|---|---|---|
| Density | g/l | n.d. |
| Absorption | % | n.d. |
| Retention | % | n.d. |
| Breaking stress | MPa | n.d. |
| Elongation at break | % | n.d. |

-continued

| Test method: | Unit | Result: |
|---|---|---|
| Modulus of elasticity | MPa | n.d. |
| Recovery time | s | 1 |
| Loss factor (tan δ) at 1 Hz | — | n.d. |
| Damping (from compression hardness) | — | 0.26 |

The invention claimed is:

1. A viscoelastic element including a polyurethane foam, obtained by reaction of a polyurethane foam reaction mixture comprising at least the following components:
   (V1) an isocyanate-functional prepolymer obtained by reaction of at least the following components:
   V1A) an aliphatic diisocyanate, and
   V1B) a di- to hexafunctional polyalkylene oxide having an ethylene oxide content of 50 to 100 mol %, based on a total amount of oxyalkylene groups present, wherein the di- to hexafunctional polyalkylene oxide comprises from 2 to 6 OH functionalities; and
   (V2) a polyurethaneurea dispersion comprising polyurethaneurea, wherein the polyurethaneurea is obtained by reacting a dispersion reaction mixture comprising at least the following components:
   V2A) an aliphatic polyisocyanate component having an average isocyanate functionality of ≥1.8 and ≤2.6,
   V2B) a polymeric polyether polyol component,
   V2C) an amino-functional chain extender component having at least 2 isocyanate-reactive amino groups, comprising at least one of an amino-functional compound C1) that does not have any ionic or ionogenic groups and an amino-functional compound C2) that has ionic or ionogenic groups,
   V2D) optionally an additional hydrophilizing component different than C2),
   V2E) optionally a hydroxy-functional compound having a molecular weight of 62 to 399 g/mol,
   V2F) optionally at least one further polymeric polyol different than V2B),
   V2G) a compound having exactly one isocyanate-reactive group or a compound having more than one isocyanate-reactive group, wherein only one of the isocyanate-reactive groups reacts with isocyanate groups present in the dispersion reaction mixture, and
   V2H) optionally an aliphatic polyisocyanate component having an average isocyanate functionality of ≥2.6 and ≤4,
   wherein the reaction of the isocyanate-functional prepolymer (V1) and the polyurethaneurea dispersion (V2) takes place in the presence of a medium containing isocyanate-reactive groups.

2. The viscoelastic element as claimed in claim 1, wherein components (V1) and (V2) are present in the polyurethane foam reaction mixture at a weight ratio of 5:1 to 1:1, based on a total weight of components (V1) and (V2).

3. The viscoelastic element as claimed in claim 1, wherein the viscoelastic element has at least one of the following properties:
   i. damping of 0.40 to 0.90, as measured according to DIN EN ISO 3386-1:2015-10;
   ii. breaking stress within a range from 0.12 MPa to 0.40 MPa, as measured according to DIN EN ISO 527-2;
   iii. elongation at break within a range from 150% to 300%, as measured according to DIN EN ISO 527-2;
   iv. water absorption of 1800% (g/g), based on dry foam weight, as measured according to DIN EN 13726-1;
   v. water retention of 80%, based on a maximum absorption;
   vi. recovery time of from 2 to 50 seconds after compression of an original volume by 50% (at a pressure of 7 kPa) to at least 90% of the original volume at standard pressure and room temperature;
   vii. volume within a range from 0.1 cm$^3$ to 1 m$^3$;
   viii. density within a range of 150 to 400 g/l;
   ix. loss factor ≥0.140, as measured according to DIN EN ISO 6721-1
   x. modulus of elasticity based on DIN EN ISO 527-2 within a range from 0.08 MPa to 0.25 MPa.

4. The viscoelastic element as claimed in claim 1, comprising component V2F), wherein components V2B) and V2F) together contain ≤30% by weight of component V2F), based on the total mass of components V2B) and V2F).

5. The viscoelastic element as claimed in claim 1, wherein component V2A) comprises at least one of isophorone diisocyanate and hexamethylene diisocyanate.

6. The viscoelastic element as claimed in claim 1, wherein component V2B) comprises a poly(tetramethylene glycol) polyether polyol.

7. The viscoelastic element as claimed in claim 1, wherein component (V1) is an isocyanate-functional prepolymer having a proportion by weight of low molecular weight, aliphatic diisocyanates having a molar mass of ≥140 to ≤278 g/mol of ≤1.0% by weight, based on the prepolymer, obtained by reaction of
   V1A) a low molecular weight, aliphatic diisocyanate of molar mass from ≥140 to ≤278 g/mol;
   V1B) a di- to hexafunctional polyalkylene oxide of OH number from ≥22.5 to ≤112 mg KOH/g and of ethylene oxide content from ≥50 to ≤100 mol %, based on the total amount of oxyalkylene groups present;
   V1C) optionally a heterocyclic 4-membered or 6-membered ring oligomer of low molecular weight, aliphatic diisocyanates having a molar mass of ≥140 to ≤278 g/mol;
   V1D) optionally a catalyst;
   V1E) optionally an alkali metal salt of an inorganic acid;
   V1F) optionally a surfactant;
   V1G) optionally a mono- or polyhydric alcohol;
   V1H) at least one of the following components:
   V1H1) one or more of a low molecular weight, aliphatic diisocyanate having a molar mass of ≥140 to ≤278 g/mol, or a polyisocyanate prepared therefrom having an isocyanate functionality of ≥2 to ≤6,
   V1H2) one or more monofunctional polyalkylene oxides having an OH number of ≥10 to ≤250 and an ethylene oxide content of ≥50 to ≤100 mol %, based on the total amount of the oxyalkylene groups present, and
   V1H3) a hydrophilic isocyanate component obtained by reaction of components V1H1) and V1H2).

8. A process for producing a viscoelastic element, comprising:
   I) mixing an isocyanate-functional polyurethane prepolymer (V1) with at least one polyurethaneurea dispersion (V2) in the presence of a medium containing isocyanate-reactive groups to obtain a polyurethane prepolymer/medium mixture;
   II) applying the polyurethane prepolymer/medium mixture from step I) to a substrate;
   III) curing the polyurethane prepolymer/medium mixture from step II) to obtain the viscoelastic element; and IV) optionally removing the viscoelastic element from the substrate.

9. The process as claimed in claim 8, wherein applying the polyurethane prepolymer/medium mixture to the substrate in step II) is performed within 3 to 90 seconds of completing the mixing in step I).

10. An earplug for insertion into an ear, comprising a viscoelastic element as claimed in claim 1.

11. A kit for producing a viscoelastic element, consisting of
(V1) an isocyanate-functional polyurethane prepolymer; and
(V2) a polyurethaneurea dispersion comprising polyurethaneurea dispersed in a medium comprising isocyanate-reactive groups.

12. The kit as claimed in claim 11, wherein component (V2) is an aqueous dispersion.

13. The kit as claimed in claim 11, wherein component (V1) is obtained by reaction of at least the following components:
V1A) an aliphatic diisocyanate, and
V1B) a di- to hexafunctional polyalkylene oxide having an ethylene oxide content of 50 to 100 mol %, based on a total amount of the oxyalkylene groups present, wherein the di- to hexafunctional polyalkylene oxide comprises from 2 to 6 OH functionalities.

14. The kit as claimed in claim 11, wherein the polyurethaneurea of the polyurethaneurea dispersion V2) is obtained by reacting at least
V2A) an aliphatic polyisocyanate component having an average isocyanate functionality of ≥1.8 and ≤2.6,
V2B) a polymeric polyether polyol component,
V2C) an amino-functional chain extender component having at least 2 isocyanate-reactive amino groups, comprising at least one of an amino-functional compound C1) that does not have any ionic or ionogenic groups and an amino-functional compound C2) that has ionic or ionogenic groups,
V2D) optionally an additional hydrophilizing component different than C2),
V2E) optionally a hydroxy-functional compound having a molecular weight of 62 to 399 g/mol,
V2F) optionally at least one further polymeric polyol different than V2B),
V2G) a compound having exactly one isocyanate-reactive group or a compound having more than one isocyanate-reactive group, wherein only one of the isocyanate-reactive groups reacts with isocyanate groups present in the dispersion reaction mixture, and optionally an aliphatic polyisocyanate component having an average isocyanate functionality of ≥2.6 and ≤4.

15. The viscoelastic element as claimed in claim 1, wherein the dispersion reaction mixture comprises V2D) the additional hydrophilizing component different than C2).

16. The viscoelastic element as claim in claim 1, wherein the dispersion reaction mixture comprises V2E) the hydroxy-functional compound having a molecular weight of 62 to 399 g/mol.

17. The viscoelastic element as claimed in claim 1, wherein the dispersion reaction mixture comprises V2F) the at least one further polymeric polyol different than V2B).

18. The viscoelastic element as claimed in claim 1, wherein the dispersion reaction mixture comprises V2H) the aliphatic polyisocyanate component having an average isocyanate functionality of ≥2.6 and ≤4.

* * * * *